United States Patent [19]

Smith et al.

[11] Patent Number: 5,776,780
[45] Date of Patent: Jul. 7, 1998

[54] METHOD FOR QUANTITATIVELY MEASURING WHITE BLOOD CELLS ESTERASE ACTIVITY IN URINE

[75] Inventors: Jack V. Smith, St. Petersburg; Jesse M. Carter, Tampa, both of Fla.

[73] Assignee: Chimera Research & Chemical, Inc., Largo, Fla.

[21] Appl. No.: 631,581

[22] Filed: Apr. 12, 1996

Related U.S. Application Data

[63] Continuation-in-part of Ser. No. 429,292, Apr. 24, 1995, Pat. No. 5,516,700, which is a continuation-in-part of Ser. No. 68,956, May 28, 1993, abandoned.

[51] Int. Cl.$^6$ .................................................. G01N 33/493
[52] U.S. Cl. .................. 436/63; 436/66; 436/904; 436/175; 436/164
[58] Field of Search .................... 436/35, 63, 66, 436/904, 164, 174–176

[56] References Cited

U.S. PATENT DOCUMENTS

| | | |
|---|---|---|
| 3,907,503 | 9/1975 | Betts et al. . |
| 4,645,842 | 2/1987 | Corey . |
| 4,704,460 | 11/1987 | Corey . |
| 4,755,472 | 7/1988 | Ismail et al. . |
| 4,758,508 | 7/1988 | Schnabel et al. . |
| 5,128,265 | 7/1992 | Meiattini . |

*Primary Examiner*—Lyle A. Alexander
*Attorney, Agent, or Firm*—Larson & Larson, P.A.; James E. Larson

[57] ABSTRACT

Detecting white blood cells in an aliquot of urine by placing the aliquot of urine in an automated analyzer sampling cup, transferring the urine to a cuvette and injecting at least one reagent composition. The reagent composition contains a buffer, an activator such as benzalkonium chloride, an indicator and at least one substance to remove substances in the urine that cause interference with colorimetric photometry. The aliquot of urine is read in accordance with a preprogrammed code at a monochromatically specified wavelength to compare absorbance of the patient's urine with a known standard containing a known concentration of white blood cells.

11 Claims, No Drawings

METHOD FOR QUANTITATIVELY MEASURING WHITE BLOOD CELLS ESTERASE ACTIVITY IN URINE

PRIOR APPLICATIONS

This application is a continuation-in-part of application Ser. No. 08/429,292, filed Apr. 24, 1995, now U.S. Pat. No. 5,516,700 which is a continuation-in-part of application Ser. No. 08/068,956, filed May 28, 1993, (now abandoned).

BACKGROUND OF THE INVENTION

This invention relates to a method and materials that are designed for use in automating urinalysis. This system is designed to analyze urine for its constituents by a method that is fully automated (does not require the use of manual methods such as refractometer, pH meter, dipsticks, or impregnated test strips). Automation as designed by this system is directed to the use of a self-operating instrument that is capable of handling multiple reagents designed for use on an automated analyzer system for the quantitative determination of white blood cells in urine.

It is known that the most common method for the analysis of urine is by the use of a manual technique known as a dipstick. This method for the analysis of urine is labor, time intensive, and costly among other detriments. The use of a dipstick for analysis of urine also relies on the subjective interpretation of the technician. The dipstick method requires the technician to submerge the dipstick in a sample of urine and remove it, wait a specified time, then compare the color development of the test on the dipstick to a color chart. Even more cumbersome methods involve the use of a refractometer, pH meter, or manual chemistry test.

The assay devices utilizing prior art includes dry tablets, dipsticks, or impregnated test strips for the analysis of urinary constituents. None of these prior devices foresees or teaches a multiple/single liquid reagent system designed specifically for auto-analyzers to analyze urinary constituents quantitatively.

One such U.S. Pat. No. 4,147,514 discloses test strips (dipsticks) for the detection of ketone bodies. The assay strips are made up of a chemical bonded to a cellulose pad on a strip. This is then dipped into a specimen sample. This method only determines ketone bodies qualitatively at its best, due to inability of the system to allow the use of standards and controls on the same strip to which the sample is applied.

Another such patent, U.S. Pat. No. 3,146,070 discloses analytical compositions in dry form on a bibulous carrier (dipstick) impregnated with a pH indicator for the determination of pH. This assay at best only determines pH qualitatively, due to the inability to use standards and controls located on the same strip for the same test sample to define and verify a quantitative determination.

Additionally, U.S. Pat. No. 4,318,709 discloses a device comprising a carrier matrix (dipstick) impregnated with the test means for specific gravity. This assay at best only determines specific gravity qualitatively, due to the inability to use standards and controls located on the same strip for the same test specimen. The prior art in this case also did not foresee the wide specimen to specimen matrix variations of real world urine samples including matrix components such as pH, and ionic strength, and the concomitant requirement of a multiple reagent system to effectively analyze urine for specific gravity in a liquid to liquid reaction. The normal pH value for a random urine can range from 4.5 to 8.0; if the prior dipstick method is used the results would be widely scattered and inaccurate without a reagent to neutralize the effect prior to completion of the assay.

Various devices are described in the literature for the determination of particular urinary constituents one by one with the use of carrier matrices (dipstick, microcapsules, filter paper, etc.). None of the prior art teaches or elucidates a means for determining by automated technology urinary constituents from a single sample of urine, via multiple tests that are reported simultaneously by an autoanalyzer using liquid reagents specifically designed for this family of instruments, and said reagents possessing detection sensitivity of clinical significance, and improved accuracy enhanced by elimination of interference to which the prior art is subject. As cited by the prior art, (in package insert literature) when evaluating laboratory test results, definitive diagnostic, or therapeutic decisions should not be based on any single result or method.

Dipsticks are affected by many substances that cause abnormal urine color including food products and supplements, and medications such as nitrofurantoin (affects the WBC assay), indican (bilirubin assay) phenylketone and phthalein-containing compounds (ketone assay), and phenazopyridine (nitrite, protein, ketone, bilirubin, and urobilinogen assays). In addition, the prior art is subject to other interfering compounds. These include:

1. glucose assay interference by ascorbic acid, ketone bodies, and high specific gravity, 2. bilirubin assay interference by, ascorbic acid, nitrite, and urobilinogen, 3. ketone body assay interference by levadopa metabolite, and sulfhydryl-containing compounds such as 2-mercaptoethane sulfonate, 4. specific gravity assay interference by protein, glucose, urea, highly buffered alkaline urine, and ketoacidosis, 5. red blood cell assay interference by captopril, microbial peroxidase, high specific gravity, nitrite, and oxidizing agents, 6. protein assay interference by highly buffered urine, alkaline urine, polyvinylpyrrolidone, skin cleansers containing chlorhexidine, and disinfectants containing quaternary ammonium groups, 7. urobilinogen assay interference by p-aminosalicylic acid, sulfonamides, p-amino benzoic acid, nitrite, and formalin, 8. nitrite assay interference by ascorbic acid, and high specific gravity, 9. white blood cell assay interference by glucose, high specific gravity, cephalexin, cephalothin, oxalic acid, gentamicin, tetracycline, and oxidizing agents.

The above noted interference compounds can cause either false positive results or false negative results.

In addition, it is clear from the above noted listings that some assays are strongly affected by other analytes of interest, and in some cases this cross reaction works across pairs. For example, high glucose will cause falsely low specific gravity results, and high specific gravity will depress glucose levels. This scenario will result in normal or low results for both glucose and specific gravity assays when the correct high "warning" results should alert the physician to the medical problems. It is also clear that some medications interfere with so many assays that the prior art is completely useless as a diagnostic tool (e.g., phenazopyridine).

In conclusion, while the prior art is subject to interference from many compounds, this invention greatly reduces or eliminates the effects of these compounds resulting in significant improvement in the patient results, and indirectly patient health.

SUMMARY OF THE INVENTION

The automated urinalysis system of this invention offers a method for reducing the consumable materials and labor costs. The system also offers increased accuracy, sensitivity, reduction of interference by substances affecting the prior art tests, and objective quantifiable determinations of urinary constituents for better diagnostic interpretation of the test results of urine, thus enabling a physician to provide better health care for the patient.

This invention improves and eliminates many of the drawbacks of the prior art yielding quantitative results, non-subjective results, reproducible results, increased accuracy, increased precision, increased sensitivity, carrier-free reagents, reagents designed for autoanalyzer use, reagents uniquely designed for each particular urine analyte assay overcoming matrix problems previously unanswered by prior art, and a method allowing vast improvement of test completion time (hundreds to thousands per hour). The present invention presents a fully automateable walk-away urinalysis system applicable to any discrete autoanalyzer currently in use, and obviously represents a marked advancement in the art of urinalysis. The clear cut object of the present invention is to provide a more comprehensive method for quantitatively determining urinary constituents of white blood cells, such method specifically yielding improved health care.

Thus, it is a primary objective of the present invention to provide techniques for determination of urinary constituents of white blood cells at low chemically significant levels.

An additional object of this invention is to make available an advanced method for analyzing a sample of urine for the quantitation of its constituents on an autoanalyzer. The advanced ability of the automated urinalysis system to offer a means for automated analysis on urine is a significant improvement in the art of urinalysis.

Additionally, the object of this invention is to provide a comprehensive method which is broadly adaptable to a wide variety of automated analyzers presently in use in the industry which will increase accuracy, sensitivity, precision, and speed. An autoanalyzer allows for precise quantitative results beyond the scope and abilities of the prior art. An autoanalyzer used in conjunction with the herein disclosed automated urinalysis reagents, provides a system that produces an objective quantitative result of an unknown urine sample obtained from a standard curve determined by analysis of standards of a known concentration run on the instrument, and verified as accurate by quantifying controls of known value. This simultaneous analysis of standards and unknowns (urine samples) yielding unbiased results improves the art of urinalysis significantly over the prior art, which yields only qualitative and subjective results.

It is a further object of this invention to provide a method for the simultaneous determination of multiple urinary components including white blood cells from a single urine sample using a system of reagents designed for autoanalyzer use. This improvement in the science of urinalysis over the prior art proves to be significant medically and economically.

Another object of this invention is to provide a method that yields quantifiable results in the determination of urinary constituents present in a sample of urine.

Yet another object of this invention is to provide uniquely formulated reagents for each urinalysis assay that were not taught or envisioned by the prior art, and overcome the inadequacies of the prior art. Consider the fact that one of the primary means of optimizing enzymic assays is identifying the best temperature, and performing the assay at that temperature. The prior art can only be used at room temperature which can vary over a wide range from test location to location, and from day to day in the same facility. Such variation adds to the imprecision, insensitivity, and inaccuracy of the prior art. Conversely, the present invention is compatible with current autoanalyzers which precisely control the temperature of the reaction cuvettes as prescribed by the assay parameters. Thus, this invention's enzyme-based and nonenzyme-based assays can be optimized for temperature thereby obtaining consistent results with even greater sensitivity, precision, and accuracy then previously possible.

Still another object of this invention is to provide a method for the determination of objective results from the photometric analysis of the automated analyzer instead of the subjective determination of human observation. The present invention provides a unique formulated reagent system that is mixed with unknown urine samples, standards, and controls and then is read spectrophotometrically with unbiased accuracy on an autoanalyzer. The use of the automated urinalysis system provides a means for improved accuracy, precision, and specificity by removal for the subjective human element from the analysis. Clearly, a system that automatically dispenses, measures, and records results is a marked improvement in the science of urinalysis.

Yet another object of this invention is to provide uniquely formulated reagents for each urinalysis assay that were not taught or envisioned by the prior art, and overcome the inadequacies of the prior art. Consider the fact that urea is the largest component of urine (besides water) by a factor of 50% over the next largest component (sodium chloride). A unique chemical formulation to compensate for urea is an advancement in the art of urinalysis. The present invention employs a liquid reagent that is not carrier dependent, designed for autoanalysis, and is not susceptible to urea and other interfering compounds in the urine sample, thus preventing interference by urea and other compounds. These improvements increase sensitivity, accuracy, and precision, thereby allowing the white blood cell assay in urine to be quantifiable.

In addition, the prior art is a matrix dependent method that cannot be used in a carrier free liquid reagent system designed for autoanalysis.

Yet another object of this invention is to provide uniquely formulated reagents for each automated urinalysis assay that was not taught or envisioned by the prior art. The assay for leukocytes in the prior art has limited accuracy and application because it is carrier dependent, it only produces qualitative results (i.e., trace, 1+, 2++, 3+++, or a range 5 to 15 leukocytes present), it yields numerous color changes (5) making objective monochromatic spectrophotometric analysis impossible, and it cannot be easily and effectively converted to a liquid matrix, which is required for use on autoanalyzers. The prior art is susceptible to interference from the sample urine matrix including but not limited to high ionic strength, antibiotics, and glucose. The prior art also takes a minimum of two minutes for color development and the following subjective interpretation of the test. The present invention is a liquid reagent that is not carrier dependent, and is specifically designed for use on autoanalyzers. The invention also uses a surfactant-activator complex that increases the sensitivity of the reagent to detect the presence of leukocyte esterase in urine. The present invention is quantitatively linear from 0.0 esterase units of activity to greater than 2000 esterase units of activity , i.e., 0 WBC's to WBC's "too numerous to count" in a high powered field of a microscope. The present invention directly measures the amount of leukocytes present by quantitatively measuring the leukocyte esterase activity in urine. This is accomplished by a colorimetric reagent specifically designed for use on an autoanalyzer, and is sensitive to leukocyte esterase. The present invention includes a compensator (buffer) for adjusting the pH of the urine samples because random samplings can range from 4.5 to 8.0. Buffering the sample is critical to obtaining optimal sensitivity, and precision by eliminating interference because leukocyte esterase activity is highest at a pH of 8.0. Due to its solid matrix, the prior art is incapable of compensating for abnormal pH resulting in its poor sensitivity and precision. The present invention has curve stabilizers and agents added to compensate for the wide variety of interfering substances found in urine, which the prior art does not teach or envision. The present invention is quantitative, carrier independent, precise, accurate and sensitive and would be an advancement in the art of urinalysis.

DETAILED DESCRIPTION OF THE INVENTION

The presently claimed method comprises a group of carrier-free liquid reagents designed for simultaneous usage on automated analyzers for quantitative determination of urinary constituents. The automated urinalysis system of the instant invention solves the problems confronting automating the analysis of urine, and in the process, represents a significant improvement over the present art. These improvements which facilitate application to automation and represent significant technical improvement over the previous art include, a buffering system for pH variation in urine by correcting pH to the analytically preferred value prior to analysis and also stabilizing reaction rates thereby improving linearity and neutralizing the interference effects of the highly complex matrix of random urines submitted for analysis. Additional technical improvement is due to the addition of components to remove interfering substances yielding reduced assay limitations and increased linearity, accuracy and precision in the resulting quantitations. These unique reagent formulations allow automation resulting in, but not limited to, enhanced speed, objectivity, accuracy and sensitivity associated with the automated test. Another technical advancement is the result of the autoanalyzer's ability to select and control the temperature of the assay. This is particularly important for assays utilizing an enzyme. A synopsis of the automated testing process follows. The entire automated urinalysis reagent system is loaded into an autoanalyzer. The controls, standards and unknown urine samples are fed into the autoanalyzer, individually mixed with each test reagent in discrete cuvettes, the absorbance read and quantitation determined by comparison with the standard curve.

The composition of each reagent of the present invention is designed for optimum reaction with the random urine samples and to effectively deal with problems arising from the tremendous variability from sample to sample due to the diet, disease state, medications, time of collection, state of hydration, sex, age and physical well being of the patient. All of the above factors can interfere with the prior art test procedures.

The automated urinalysis system reagents are individually designed for optimum analysis of specific urinary components. The reagent system for leukocytes (WBC) in urine is carrier-independent and has specific agents added to compensate for interference caused by enzyme inhibitors, oxalic acid, high ionic strength urines (specific gravity), glucose, antibiotics (Tetracycline), cephalexin, cephalothin, abnormal pH values and other normal urinary constituents. The reagent system is composed of a single reagent, but can be a two-reagent system. This reagent system is specifically designed for matrix interference neutralization and automated liquid reagent compatibility. Examples of compounds that would act as interfering substrates that would yield false positive results with the prior art, but not with the present invention include 3-indoyl acetate, p-nitrophenyl stearate, phenyl laurate, N-toluene sulfonyl alanine indole ester, derivatized pyrrole amino acid ester or other active esters in random urine specimens. Ethylenediaminetetraacetic acid (disodium salt), 2,3-butanedione monoxime, and dimercaptopropanol are components that can be added to the reagent and used to neutralize interfering substances by chelating, removing enzyme inhibitors, and acting as a solution clarifier. They cause the disappearance of the characteristic yellow color of urine, thereby enhancing spectrophotometric analysis. These interference neutralizing compounds can be added to the reagent to react competitively with the interfering substances and enhance leukocyte esterase activity. The reagent may also contain bile salts, albumin, and calcium ions (calcium chloride) to increase esterase activity. Other enzyme activators are added such as calcium chloride or magnesium chloride. These agents act to enhance activity of the esterase as well as prevent denaturation of the enzyme. The reagent may also contain hydrogen peroxide as a substrate (oxygen donor) for peroxidase. Peroxidase and hydrogen peroxide interact to yield an oxygen radical. This radical acts to enhance the color developing properties (speed, completeness of reaction, etc.) of the reagent system. Sodium azide is present as a hydrogen peroxide stabilizer. The reagent also contains a buffer to adjust sample pH and aid in solubility and compatibility of the reagent's complex chemical matrix. This complex chemical matrix requires a complementary aqueous buffering system with unique dynamics capable of adjusting the reaction solution to the ideal pKa, and pH of approximately 7 to 9 and promoting reagent component compatibility with autoanalyzers. Unbuffered solutions may have high acidic or basic activity, or strictly organic properties which are not compatible with autoanalyzer syringes, tubing, metal and plastic parts. This reagent also contains benzalkonium chloride, a surfactant that enhances the carrier-free matrix, decreases surface tension, promotes effective mixing on a molecular level and improves flow dynamics through tubing and syringes of automated analyzers. Benzalkonium chloride (BAC) has the unique ability to activate and enhance the reaction as well as perform the duties of a surfactant. A number of other compounds can be substituted for BAC that perform this dual role of activator and surfactant including 2,5-dimethylbenzene sulfonic acid, benzethonium chloride, cetyltrimethylammonium bromide, brij-35 (polyoxyethylene (23) lauryl ether), Triton X 405 (octylphenyl-polyethylene glycol ethers), 3,5-dimethylhexyn-3-ol, n-Octyl-B-glucopyranoside, polyethylene glycol 6000 and 20000, Tween 20 (polyoxyethylene (20) sorbitan monolaurate) and 80 (polyoxyethylene (20) sorbitan monooleate), Myrj 52 (polyoxyl 40 stearate), Triton×100 (octoxynal), Triton WR1339 (tyloxapol), Lutensol ED 370, Pluronic PE 4300, 6100, 6200, 6400, 6800, and 10500 ($\alpha$-hydro-$\omega$-hydroxypoly (oxyethylene) poly (oxypropylene)-poly (oxyethylene) copolymer), and Plurafac LF400, LF401, LF600, and LF711. Not all surfactants will activate and enhance the reaction. Sodium dodecylsulfate will slow the reaction or inhibit it. Furthermore, not all activators will perform the tasks of a surfactant. The following compounds act only as surfactants: Ammonium perfluoroalkylsulfonates, nonionic fluoroaliphatic polymeric esters, and sodium dodecyl sulfate. The following compounds act only as activators: acetonitrile, and bile salts. It should be pointed out that this reagent requires an activator and a surfactant. These roles can be filled by a single compound that does both, or by two distinct compounds, each performing one task.

The concentration of reagent buffers and other components can be varied to compensate for limitations and variations in the configuration of sampling and reagent delivery systems of various makes of autoanalyzers. The reagent buffers also compensate for abnormal pH of urine samples and urines with high buffer capacities.

The reagent system for leukocytes (WBC's) may consist of a single reagent, or a dual reagent system. The color generating mechanism or indicator of the reagent system is the same for the single or dual system and is the result of leukocyte esterase acting upon compatible esters. This ester/esterase reaction produces a relatively unstable indoxyl moiety that is oxidized to form an indigo color that is monitored by monochromatic spectrophotometry. The addition of dehydrogenase to the reagent will enhance the speed of reaction and completeness of the reaction of the indoxyl moiety. The dehydrogenase oxidizes the alcohol group on the indoxyl group and promotes formation of a ketone. This transitional indoxyl ketone radical enhances color development, specificity, and accuracy and sensitivity of the reaction. The reagent system may contain one or more of the following compounds, 2,4-dinitrophenylhydrazine, hydroxylamine, or semicarbizide, which in the presence of indoxide ketones will give color development that can be monitored at the same wavelength as the indigo. A further enhancement of the method concerning the indoxyl intermediate, is the addition of p-dimethylaminobenzaldehyde or p-nitrobenzenediazonium tetrafluroborate or other azo indicators.

The indicators for the detection of leukocytes esterase in urine have the formula:

A1-A2 . . . -X wherein A1- is an amino acid

A2 . . . is an additional amino acid linked to A1-

-X is a chromophore from the following group: nitrophenyl, nitroanilide, NH2, thiobenzyl ester, naphthylamide, N-t-butylamide, N-ethylamide, N-methylamide, benzyl ester, t-butyl ester, methyl ester, ethyl ester, hexyl ester, N,N-dimethylamide, 7-amido-4-methylcoumarin ester, fluorescein, diazide, diazonium, and trifluoroacetate.

Typical of the indicators are: t-butyloxycarbonyl-ala-p-nitrophenyl ester, t-butyloxycarbonyl-ala-nitroanilide, suc-ala-ala-ala-nitronilide, acetyl-ala-ala-pro-val-nitroanilide, methoxysuccinyl-suc-ala-ala-pro-val-nitroanilide, methoxysuccinyl-suc-ala-ala-pro-ala-nitroanilide, methoxysuccinyl-suc-ala-ala-pro-met-nitroanilide, benzyloxycarbonyl-ala-2-nitroanilide, t-butyloxycarbonyl-ala-2=-nitroanilide, methoxysuccinyl-ala-ala-pro-val-nitrophenyl, benzyloxycarbonyl-val-p-nitrophenyl, methoxysuccinyl-ala-ala-pro-ala-thiobenzyl ester, indoxylcarboxylic acid ester, methoxysuccinyl-ala-ala-pro-val-thiobenzyl ester, methoxysuccinyl-ala-pro-ala-thiobenzyl ester, methoxysuccinyl-ala-pro-val-thiobenzyl ester, methoxysuccinyl-ala-pro-val-thiobenzyl ester, t-butyloxycarbonyl-ala-ala-ala-thiobenzyl ester, t-butyloxycarbonyl-ala-ala-val-thiobenzyl ester, benzyloxycarbonyl-ala-p-nitrophenyl, methoxysuccinyl-ala-pro-ala-nitroanilide,methoxysuccinyl-ala-pro-val-nitroanilide, suc-ala-ala-ala-nitroanilide, suc-ala-ala-val-nitroanilide, acetyl-ala-ala-pro-val-NH2, acetyl-ala-ala-pro-val-NH2, n-suc-ala-ala-val-p-nitroanilide, suc-ala-ala-ala-phe-nitroanilide, suc-ala-ala-ala-phe-nitroanilide, suc-ala-ala-phe-nitroanilide, acetyl-ala-ala-pro-phe-nitroanilide, hydrochloride-H-ala-ala-pro-phe-nitroanilide, methoxysuccinyl-suc-ala-ala-pro-phe-nitroanilide, suc-ala-ala-pro-phe-nitroanilide, glt-ala-ala-pro-phe-nitroanilide, mal-ala-ala-pro-phe-nitroanilide, HBrNH2(CH2)5CO-ala-ala-pro-phe-nitroanilide, suc-ala-pro-leu-nitroanilide, suc-ala-pro-leu-phe-nitroanilide, methoxysuccinyl-suc-ala-ala-pro-met-nitroanilide and methoxysuccinyl-suc-ala-lle-pro-met-nitroanilide.

These will react with the intermediate to enhance color development that can then be monitored at a wavelength that is specific for the indicator complex used. This monitored wavelength can vary from 340 nm to 700 nm depending on which indicator is used. This reaction would enhance specificity, sensitivity and accuracy. The reagent is buffered depending on which group or single component is used in the color developing reagent.

The second reagent mix (R2), if applicable, also contains a buffer to adjust sample pH and to aid in solubility and compatibility of the R2's complex chemical matrix. This complex reagent matrix requires a complementary aqueous buffering system with unique dynamics capable of adjusting the reaction solution to the ideal pKa and pH between 7 and 9, and promoting component solution compatibility with autoanalyzers. Unbuffered solutions may have high acidic, or basic activity, or strictly organic properties which are not compatible with autoanalyzer syringes, tubing, metal and plastic parts. This reagent system buffering is designed to correct these problems. The R2 also contains surfactants to decrease surface tension, promote effective mixing on a molecular level, and improve flow dynamics through tubing and syringes of automated analyzers. The following components and concentration of components of R1 and/or R2 reagents can be varied to compensate for limitations and variations in the configuration of sampling and reagent delivery systems of various makes of autoanalyzers.

Without further elaboration, it is believed that one skilled in the art can, using the following description, effectively utilize the present invention. The following preferred specific embodiments are, therefore, to be construed as merely illustrative and not limitive of the remainder of the disclosure of the present invention in any way whatsoever. In the following examples, all instrument parameters, reagent combinations and method techniques are set forth.

EXAMPLE 1

The automated WBC urinalysis reagent system's single reagent system contains the dual surfactant activator, benzalkonium chloride, ethylenediaminetetraacetic acid, 3-indoyl acetate and buffer. The reagent is then placed in the autoanalyzer. The urine sample, standards and controls are placed in the autoanalyzer specimen cups. The urine samples, standards and controls are aliquoted from the cups into cuvettes, mixed with the reagent and read at specified intervals as dictated by the instrument parameters at the specific wavelength (monochromatically) depending on reagent combination used. In this instance the assay should be read at 660 nanometers with read times specific to the analyzer. The optimum analyzer temperature is set at 37° C.

EXAMPLE 2

The automated WBC urinalysis reagent system's first reagent (R1) contains the dual surfactant activator, benzalkonium chloride, buffer, 2,3-butanedione monoxime, and peroxidase. The second reagent (R2) consists of some or all of the following: hydrogen peroxide, N-toluene sulfonyl alanine indole ester, pyrrole amino acid ester, buffers and/or surfactants. The reagents are placed on the autoanalyzer. The urine samples, standards and controls are placed in the autoanalyzer specimen cups. The urine samples, standards and controls are aliquoted from the cups into cuvettes mixed with the first reagent, the second reagent is then added and mixed and the solutions are then read at specified intervals as dictated by the instrument parameters at the specific wavelength (monochromatically) depending on the reagent combination used. In this instance, the assay should be read at 405 nanometers with read time specific to the analyzer. The optimum analyzer temperature is set at 30° C.

EXAMPLE 3

The automated WBC urinalysis reagent system's first reagent (R1) contains the dual surfactant activator, 2,5-dimethylbenzene sulfonic acid, buffer, calcium chloride, dimercaptopropanol. The second reagent (R2) consists of some or all of the following: dehydrogenase, 3-indolyl acetate, N-toluene sulfonyl alanine indole ester, derivatized pyrrole amino acid ester, buffers and/or surfactants. The reagents are placed on the autoanalyzer. The urine samples, standards and controls are aliquoted from the cups into cuvettes and mixed with the first reagent. The second reagent is then added and mixed and the solutions are then read at specified intervals as dictated by the instrument parameters at the specific wavelength (monochromatically) depending on the reagent combination used. In this instance, the assay should be read at 600 nanometers with read time specific to the analyzer. The optimum analyzer temperature is set at 37° C.

EXAMPLE 4

The automated WBC urinalysis reagent system's first reagent (R1) contains some or all of the following: surfactant activator, benzethonium chloride, buffer, albumin, ethylenediaminetetraacetic acid, 3-indolyl acetate, N-toluene sulfonyl alanine indole ester, and derivatized pyrrole amino acid ester. The second reagent (R2) consists of some or all of the following: dehydrogenase, 2,4-dinotrophenylhydrazine, buffers and surfactants. The reagents are placed on the autoanalyzer. The urine samples, standards and controls are placed in the autoanalyzer specimen cups. The urine samples, standards and controls are aliquoted from the cups into cuvettes and mixed with the first reagent. The second reagent is then added and mixed and the solutions are then read at specified intervals as dictated by the instrument parameters at the specific wavelength (monochromatically) depending on the reagent combination used. In this instance, the assay should be read at 405 nanometers with read time specific to the analyzer. The optimum analyzer temperature is set at 37° C.

EXAMPLE 5

The automated WBC urinalysis reagent system's first reagent (R1) contains some or all of the following: a surfactant (ammonium perfluoroalkyl sulfonate), buffer, an activator (bile salts), and 2,3-butanedione monoxime. The second reagent (R2) consists of some or all of the following: p-dimethylaminobenzaldehyde, 3-indolyl acetate, N-toluene sulfonyl alanine indole ester, amino acid ester, buffers, dilute hydrochloric acid and surfactants. The reagents are placed on the autoanalyzer. The urine samples, standards and controls are placed in the autoanalyzer specimen cups. The urine samples, standards and controls are aliquoted from the cups into cuvettes and mixed with the first reagent. The second reagent is then added and mixed and the solutions are then read at specified intervals as dictated by the instrument parameters at the specific wavelength (monochromatically) depending on the reagent combination used. In this instance, the assay should be read at 400 to 660 nanometers depending on which R2 indicator is employed with read time specific to the analyzer. The optimum analyzer temperature is set at 30° C.

EXAMPLE 6

The automated WBC urinalysis reagent system's first reagent (R1) contains some or all of the following: surfactant activator BAC, buffer, 2,3-butanedione monoxime, ethylenediaminetetraacetic acid, bile salts, calcium chloride, and/or albumin. The second reagent (R2) consists of some or all of the following: p-nitrophenyl stearate, phenyl laurate, buffers and surfactants. The reagents are placed on the autoanalyzer. The urine samples, standards and controls are placed in the autoanalyzer specimen cups. The urine samples, standards and controls are aliquoted into cuvettes, mixed with the first reagent, the second reagent is then added and mixed and the solutions are then read at specified intervals as dictated by the instrument parameters at the specific wavelength (monochromatically) depending on the reagent combination used. In this instance, the assay should be read at 405 nanometers with read time specific to the analyzer. The optimum analyzer temperature is set at 37° C.

EXAMPLE 7

Liquid reagent is successfully compounded by dissolving into water the following chemicals at room temperature (25 degree C.):
Solution RI (Reagent 1)
1.2M TRIS buffer, pH 7.00 anti-leukocyte antibody (1:250 dilution in distilled water) 2.0 ml distilled water added to 100.0 ml total volume of solution. Solution R2 contains 1.2 molar tris buffer and 1.70 g/liter of NAD.

This assay is based on competition between leukocytes in the urine sample and leukocyte protein labeled with the enzyme glucose-6-phosphate dehydrogenase (G6P-DH) for antibody binding sites. Enzyme activity decreases upon binding to the antibody, so the leukocyte concentration in the urine sample can be measured in terms of enzyme activity. Active enzyme converts oxidized nicotinamide adenine dinucleotide (NAD) to its reduced form NADH resulting in an absorbance change that is measured spectrophotometrically at 340 nm. The leukocyte antibody can be specific for a particular protein found in the leukocyte or on its cell membrane.

A sample of leukocyte-containing urine is obtained which, upon mixing with the liquid reagent, gives a measurable response after about 5 to 20 seconds. The sensitivity is about to 1.0 leukocytes/uL or the corresponding amount of leukocyte protein. A smaller number of intact leukocytes can under certain circumstances, still bring about a measurable response with the automated liquid chemistry test. This method for detecting white blood cells in urine includes placing an aliquot of the sample urine, standards, and controls to be tested in automated analyzer sampling cups, placing the cups in a sampling tray within the automated analyzer, transferring aliquots of the urine sample, standards and controls into cuvettes mounted within the automated analyzer, injecting at least one reagent composition in an aqueous medium into the cuvettes, and reading the sample reagent complex at specified intervals, in accordance with a preprogrammed code introduced into the automated analyzer, Instrument Parameters (Hitachi 717):

| CHEMISTRY PARAMETERS | |
|---|---|
| TEST | [URINE WBC] |
| ASSAY CODE | [1 POINT] : [0] - [50] |
| SAMPLE VOLUME | [10] |
| R1 VOLUME | [300] [100] [NO] |
| R2 VOLUME | [ 0] [100] [NO] |
| WAVE LENGTH | [700] [340] |
| CALIB. METHOD | [LINEAR] [0] [0] |
| STD. (1) CONC. -POS. | [ 0] - [1] |
| STD. (2) CONC. -POS. | [ 100] - [2] |
| STD. (3) CONC. -POS | [ 0] - [3] |
| STD. (4) CONC. -POS. | [ 0] - [0] |
| STD. (5) CONC. -POS | [ 0] - [0] |
| STD. (6) CONC. -POS. | [ 0] - [0] |
| SD LIMIT | [ 999] |
| DUPLICATE LIMIT | [32000] |
| SENSITIVITY LIMIT | [ 0] |
| ABS. LIMIT (INC/DEC) | [32000] [INCREASE] |
| PROZONE LIMIT | [ 0] [UPPER] |
| EXPECTED VALUE | [ 0] - [ 1.0] |
| TECH. LIMIT | [ 0] - [ 100] |
| INSTRUMENT FACTOR | [ 1.0] | at a preprogrammed monochromatically specified wavelength, to compare absorbance of the urine and reagent composition complex with that of a standard containing a known concentration of white blood cells and thereby determining the presence or absence of white blood cells in the urine. The optimum analyzer temperature is set at 37° C.

EXAMPLE 8

Liquid reagent is successfully compounded by dissolving into water the following chemicals at room temperature (25 degree C.):

Solution RI (reagent 1)

0.1M TRIS buffer, pH 8.00

0.1% Benzalkonium chloride, the surfactant/activator 0.0001M N-methoxysuccinyl-ala-ala-ala-pro-val p-Nitroanalide, the indicator A sample of leukocyte-containing urine is obtained which, upon mixing with the liquid reagent, gives a measurable response after about 5 to 20 seconds. The sensitivity is about to 1.0 leukocytes/uL or the corresponding amount of leukocyte protein. A smaller number of intact leukocytes can under certain circumstances, still bring about a measurable response with the automated liquid chemistry test. This method for detecting white blood cells in urine includes placing aliquots of the urine samples, standards, and controls to be tested in automated analyzer sampling cups, placing the cups in a sampling tray within the automated analyzer, transferring aliquots of the urine samples, standards, and controls to cuvettes mounted within the automated analyzer, injecting at least one reagent composition in an aqueous medium into the cuvettes, the reagent composition containing the above buffer to adjust the pH of the urine to a preferred value, together with the activator surfactant and the above indicator or other indicator such as N-methoxysuccinyl-amino acid esters, to quantitatively determine white blood cells in the urine, and reading the sample of urine at specified intervals, in accordance with a preprogrammed code introduced into the automated analyzer Instrument Parameters (Hitachi 717)

| CHEMISTRY PARAMETERS | |
|---|---|
| TEST | [URINE WBC] |
| ASSAY CODE | [1 POINT] : [0] - [50] |
| SAMPLE VOLUME | [10] |
| R1 VOLUME | [300] [100] [NO] |
| R2 VOLUME | [ 0] [100] [NO] |
| WAVE LENGTH | [700] [415] |
| CALIB. METHOD | [LINEAR] [0] [0] |
| STD. (1) CONC. -POS. | [ 0] - [1] |
| STD. (2) CONC. -POS. | [ 100] - [2] |
| STD. (3) CONC. -POS | [ 0] - [0] |
| STD. (4) CONC. -POS. | [ 0] - [0] |
| STD. (5) CONC. -POS | [ 0] - [0] |
| STD. (6) CONC. -POS. | [ 0] - [0] |
| SD LIMIT | [ 999] |
| DUPLICATE LIMIT | [32000] |
| SENSITIVITY LIMIT | [ 0] |
| ABS. LIMIT (INC/DEC) | [32000] [INCREASE] |
| PROZONE LIMIT | [ 0] [UPPER] |
| EXPECTED VALUE | [ 0] - [ 1.0] |
| TECH. LIMIT | [ 0] - [ 100] |
| INSTRUMENT FACTOR | [ 1.0] | at a preprogrammed monochromatically specified wavelength, to compare absorbance of the urine and reagent composition complex with that of a standard containing a known concentration of white blood cells and thereby determining the presence or absence of white blood cells in the urine. In this case the preferred wavelength is about 415 nm. The optimum analyzer temperature is set at 37° C. It is known that substitutes for the amino acid derivative indicator substrate in this example (N-methoxysuccinyl-ala-ala-ala-pro-val-p-nitranalide) include amino acid esters, and 3-indolz-ol-n-toluene sulfonyl alanine indole ester. Furthermore, substitutes for the tris buffer in this example could include any buffer material with an effective range from 6 to 10 pH units.

From the foregoing, it is believed that those familiar with the art will readily recognize and appreciate the novel concepts and features of the present invention. Numerous variations, changes and substitutions of equivalents will present themselves to persons skilled in the art and may be made without necessarily departing from the scope and principles of this invention. Therefore, the invention has been described with reference to a number of its embodiments, it can nevertheless be arbitrarily varied within the scope of the following claims.

We claim:

1. A method for quantitatively measuring white blood cell esterase activity in a patient's urine comprising placing an aliquot of the urine to be tested in an automated analyzer sampling cup, placing the cup in a sampling tray within the automated analyzer, transferring the urine to a cuvette mounted within the automated analyzer, injecting at least one reagent composition in an aqueous medium into the cuvette, wherein said at least one reagent composition comprises a buffer to adjust the pH of the urine to 7 to 9, an activator and surfactant selected from the group consisting of benzalkonium chloride, 2,5-dimethylbenzene sulfonic acid, and benzethonium chloride, and an indicator to determine leucocyte esterase activity in the patient's urine, reading the aliquot of urine at specified intervals, in accordance with a preprogrammed code introduced into the automated analyzer, at a preprogrammed monochromatically specified wavelength, to compare absorbance of the patient's urine and reagent composition complex with that of a standard containing a known concentration of leucocyte esterase and thereby determining the quantitative amount of leucocyte esterase in the patient's urine.

2. The method according to claim 1 wherein there is a first and second reagent composition in an aqueous medium injected into the cuvette.

3. The method according to claim 1 wherein the wavelength of the analyzer is about 340 to 700 nanometers.

4. The method according to claim 1 wherein said at least one reagent composition further comprises a first reagent composition comprising a buffer to adjust the pH of the urine to 7–9, benzalkonium chloride, and a second reagent composition comprising a buffer, and an indicator compound selected from the group consisting of anti-leukocyte antibody, 3-indolyol acetate, N-toluene sulfonyl alanine indole ester, and methoxysuccinyl-ala-ala-ala-pro-val-p-nitroanalide.

5. The method according to claim 1 wherein the activator is benzalkonium chloride.

6. The method according to claim 1 wherein the activator is 2,5-dimethylbenzene sulfonic acid.

7. The method according to claim 2 wherein the first reagent composition contains benzalkonium chloride.

8. The method according to claim 3 wherein the activator is benzalkonium chloride.

9. The method according to claim 1 wherein said at least one reagent composition further comprises a first reagent composition containing a compound to remove substances in the urine that cause interference with calorimetric photometry selected from the group consisting of albumen, calcium chloride, dimercaptopropanol, 2,3,-butadione monoxime and ethylenediamine-tetraacetic acid.

10. A method according to claim 1 wherein the activator and surfactant is benzalkonium chloride, and the indicator is methoxysuccinyl-ala-ala-ala-pro-val-p-nitroanalide.

11. The method according to claim 1 wherein the indicator is selected from the group consisting of t-butyloxycarbonyl-ala-p-nitrophenyl ester, t-butyloxycarbonyl-ala-nitroanilide, suc-ala-ala-ala-nitroanilide, acetyl-ala-ala-pro-val-nitroanilide, methoxysuccinyl-suc-ala-ala-pro-val-nitroanilide, methoxysuccinyl-suc-ala-ala-pro-ala-nitroanilide, methoxysuccinyl-suc-ala-ala-pro-met-nitroanilide, benzyloxycarbonyl-ala-2-nitroanilide, t-butyloxycarbonyl-ala- 2-nitroanilide, methoxysuccinyl-ala-ala-pro-val-nitrophenyl, benzyloxycarbonyl-val-p-nitrophenyl, methoxysuccinyl-ala-ala-pro-ala-thiobenzyl ester, indoxylcarboxylic acid ester, methoxysuccinyl-ala-ala-pro-val-thiobenzyl ester, methoxysuccinyl-ala-pro-ala-thiobenzyl ester, methoxysuccinyl-ala-pro-val-thiobenzyl ester, t-butyloxycarbonyl-ala-ala-ala-thiobenzyl ester, t-butyloxycarbonyl-ala-ala-val-thiobenzyl ester, benzyloxycarbonyl-ala-p-nitrophenyl, methoxysuccinyl-ala-pro-ala-nitroanilide, methoxysuccinyl-ala-pro-val-nitroanilide, suc-ala-ala-ala-nitroanilide, suc-ala-ala-val-nitroanilide, acetyl-ala-ala-pro-val-NH2, acetyl-ala-ala-pro-val-NH2, N-suc-ala-ala-val-p-nitroanilide, suc-ala-ala-ala-phe-nitroanilide, suc-ala-ala-ala-phe-nitroanilide, suc-ala-ala- phe-nitroanilide, acetyl-ala-ala-pro-phe-nitroanilide, hydrochloride-H-ala-ala-pro-phe-nitroanilide, methoxysuccinyl-suc-ala-ala-pro-phe-nitroanilide, suc-ala-ala-pro-phe-nitroanilide, glt-ala-ala-pro-phe-nitroanilide, mal-ala-ala-pro-phe-nitroanilide, HBrNH2(CH2)5CO-ala-ala-pro-phe-nitroanilide, suc-ala-pro-leu-nitroanilide, suc-ala-pro-leu-phe-nitroanilide, methoxysuccinyl-suc-ala-ala-pro-met-nitroanilide and methoxysuccinyl-suc-ala-ile-pro-met-nitroanilide.

* * * * *

UNITED STATES PATENT AND TRADEMARK OFFICE
CERTIFICATE OF CORRECTION

PATENT NO. : 5,776,780
DATED : July 7, 1998
INVENTOR(S) : Jack V. Smith et al.

It is certified that error appears in the above-identified patent and that said Letters Patent is hereby corrected as shown below:

Title page,
Item [63], Related U.S. Application Data, please delete "continuation-in-part of Ser. No. 68,956" and insert -- continuation of Ser. No. 68,956 --.

Column 1,
Line 8, please delete "continuation-in-part" and insert -- continuation --.

Column 13,
Line 32, please delete "calorimetric" and insert -- colorimetric --.

Signed and Sealed this

Twenty-seventh Day of November, 2001

Attest:

Nicholas P. Godici

Attesting Officer

NICHOLAS P. GODICI
Acting Director of the United States Patent and Trademark Office